(12) United States Patent
Haley

(10) Patent No.: US 12,016,707 B2
(45) Date of Patent: Jun. 25, 2024

(54) BIG DATA 911™—EXPEDITED EMT RESPONSE AFTER VEHICLE ACCIDENTS OR OTHER EMERGENCIES

(71) Applicant: Mark Haley, Mckinney, TX (US)

(72) Inventor: Mark Haley, Mckinney, TX (US)

( * ) Notice: Subject to any disclaimer, the term of this patent is extended or adjusted under 35 U.S.C. 154(b) by 0 days.

(21) Appl. No.: 17/302,264

(22) Filed: Apr. 29, 2021

(65) Prior Publication Data

US 2022/0346728 A1   Nov. 3, 2022
US 2024/0074711 A9   Mar. 7, 2024

Related U.S. Application Data

(63) Continuation-in-part of application No. 16/852,505, filed on Apr. 19, 2020.

(51) Int. Cl.
| | |
|---|---|
| A61B 5/00 | (2006.01) |
| G16H 10/60 | (2018.01) |
| H04M 3/22 | (2006.01) |
| H04W 4/029 | (2018.01) |
| H04W 4/16 | (2009.01) |
| H04W 4/44 | (2018.01) |
| H04W 4/90 | (2018.01) |

(52) U.S. Cl.
CPC ............ *A61B 5/747* (2013.01); *G16H 10/60* (2018.01); *H04M 3/2218* (2013.01); *H04W 4/029* (2018.02); *H04W 4/16* (2013.01); *H04W 4/44* (2018.02); *H04W 4/90* (2018.02); *A61B 5/0022* (2013.01)

(58) Field of Classification Search
None
See application file for complete search history.

(56) References Cited

U.S. PATENT DOCUMENTS

| | | | |
|---|---|---|---|
| 7,724,889 B2 | 5/2010 | Bushey et al. | |
| 8,238,532 B1 | 8/2013 | Cox et al. | |
| 10,276,190 B2 | 4/2019 | Ashoori et al. | |
| 10,453,011 B1* | 10/2019 | Briggs | G06Q 20/405 |
| 10,992,805 B1* | 4/2021 | Johnson | H04M 3/5116 |
| 2013/0332026 A1* | 12/2013 | McKown | B60R 21/013 |
| | | | 701/33.7 |
| 2022/0068137 A1* | 3/2022 | Nagasawa | G08G 1/162 |

* cited by examiner

*Primary Examiner* — Adolf Dsouza

(57) ABSTRACT

Device, system, and method, for simplicity call Big Data 911™, which expedites 911 call response times after vehicle accidents or other emergencies. It uses GPS and other data which automatically detects a crash and sends this data comprising the location, severity of the crash, etc., to the cloud using software and/or hardware such as a phone app or device on the vehicle. This data also identifies the victim with all relevant medical or other records. This ensures that during the crucial Golden Hour after the accident EMTs (Emergency Medical Technicians), police and other responders provide the optical medical treatment both en route to the hospital and once there. This includes the technology to initiate the 911 call combined with AI or statistical information in the cloud to expedite the ideal medical solution for the victim. This system can be used nationally or internationally as a person travels worldwide.

4 Claims, 4 Drawing Sheets

BIG DATA 911™—EXPEDITED EMT RESPONSE AFTER VEHICLE ACCIDENTS OR OTHER EMERGENCIES

This application is a continuation-in-part application of and claims priority to U.S. patent application Ser. No. 16/852,505 (filed Apr. 19, 2020 "Automatic Ejection Safety Technology with a Skydiving Simulator for Improving Pilot Safety", the disclosure of which is incorporated herein by reference in its entirety.

TECHNICAL FIELD

Device, system, and method which expedites EMTs (Emergency Medical Technicians) response times after vehicle accidents by automatically initiating a 911 computer call or other call from a vehicle and also identifying the victim using voice or facial recognition. This would ensure the optimum medical response customized for the victim during the crucial Golden Hour after the accident. The goal is to expedite transportation to a hospital and immediately identify the victim to ensure appropriate medical treatments.

BACKGROUND

This invention, the Big Data 911™ Expedited Targeted Emergency Healthcare system, improves the response to medical emergencies anywhere, such at home or in vehicle crashes, thereby ensuring the ideal medical care after an accident. There were 36.560 U.S. traffic deaths in 2018 and faster emergency team response times could improve the chances for survival of hundreds or even thousands of accident victims each year. In 2018, 10% of fatal crashes were reported in over ten minutes. This invention identifies technologies and economic incentives so that drivers permit sharing crash data automatically during the seconds leading to an accident.

In 2018, only 10% of U.S. drivers permitted sharing telematic vehicle data, the key info on the vehicle's speed, location, acceleration, etc. However, with larger automobile insurance discounts, more privacy protections and better technology, more drivers could be enticed to share this data thereby expediting response times and improving the chances for survival of accident victims. The European Union is far ahead of the US since after April 2018 all European Car Makers have been required to include eCall, an automated emergency call technology.

This patent identifies the best options of using Big Data to expedite the response times of first responders after traffic accidents thereby potentially saving lives or reducing injuries. On crowded urban U.S. roads many people immediately call 911 after an accident. Some cars even automatically send out distress calls. However late at night and in remote areas, the accident may not be reported for hours. This invention focuses on using Big Data to automatically report those accidents during the seconds leading up to a crash, rather than 10 minutes after the accident. Today's newest car sensors collect terabytes of data each day some of which are used to autonomously drive the car or even brake in potential accidents. This invention focuses on how to ensure that key parts of this data is sent to the cloud to alert first responders immediately after an accident.

"Golden Hour"—It's Crucial to Expedite Treatment within an Hour to Save Lives

Per the American College of Surgeons, the idea of the "Golden Hour" highlights the crucial need to successfully treat a patient in the first 60 minutes after a major injury such as an automobile crash or a gunshot wound. The method of treating trauma is called the "Advanced Trauma Life Support (ATLS)." It was developed in 1976 based on experiences treating those seriously injured during the Vietnam war and in dangerous U.S. cities.

DETAILED DESCRIPTION

This invention offers an integrated method of responding to vehicle accidents or general 911 calls so that EMTs know the entire medical background of the patient and can therefore provide appropriate treatment immediately en route to the hospital. The goal is to expediate moving the victim to the hospital and to provide the ideal medical treatment in Golden Hour after an accident to ensure the best medical outcome. For vehicle accidents, a device, ideally mandated by the government similar to the mandate for smoke alarms, would automatically send out a distress call to 911 as the vehicle data indicated an impeding crash. This call would be just prior to impact in case it is a massive wreck which disables all communications and/or on-board computers. The information could even include the identity of the driver using cameras which monitor the driver as part of the autonomous driving system for the latest vehicles.

Figure 1:
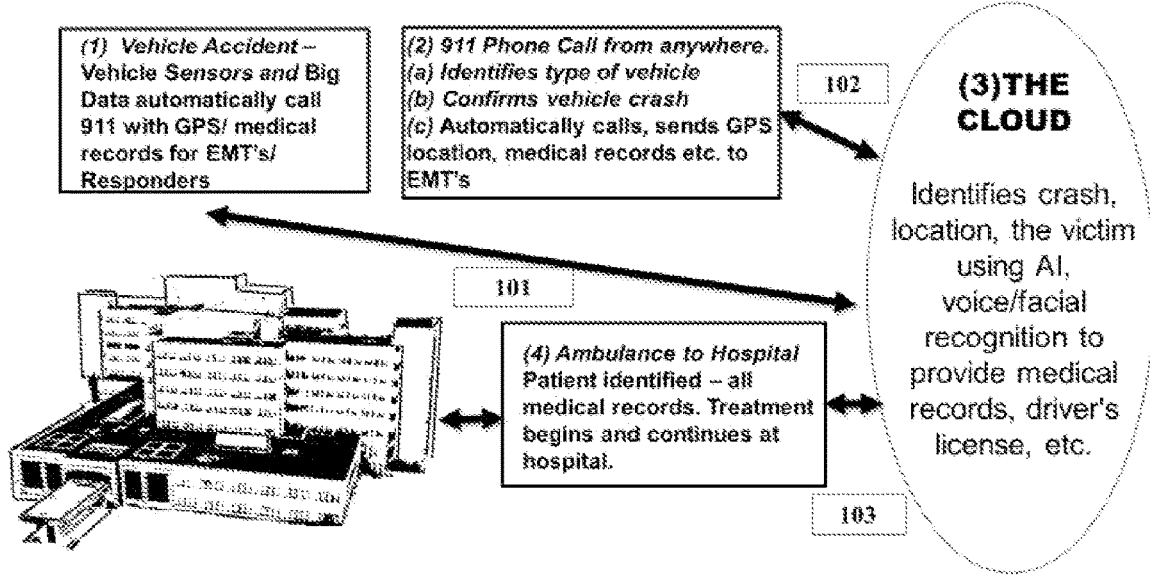
FIG. 1 Overview Flow Chart logic of the Claims.

In FIG. 1, Block 1, if it is a vehicle accident, then with the onboard device, it automatically calls 911, sends GPS location, crash information and medical records to EMT's en route. If it's a non-vehicle emergency, such as a general 911 from a home, then Block 2 Voice recognition identifies the victim with related medical records, prior 911 calls, and other relevant information.

Using this technology, in either a vehicle accident or a 911 call from home, the identity and medical background of the victim is known. Therefore, the EMTs can customize the treatment of the patient en route to the hospital. Block 3—using facial or voice recognition or caller ID info, the victim's medical records are available from Big Data in the cloud with Artificial Intelligence (AI) constantly reviewing the appropriate medical issues and treatments. While being transported to the hospital, Block 4, this system has identified the patient with related medical histories so the EMTs can provide initial customized treatment which would continue at the hospital.

Figure 2:
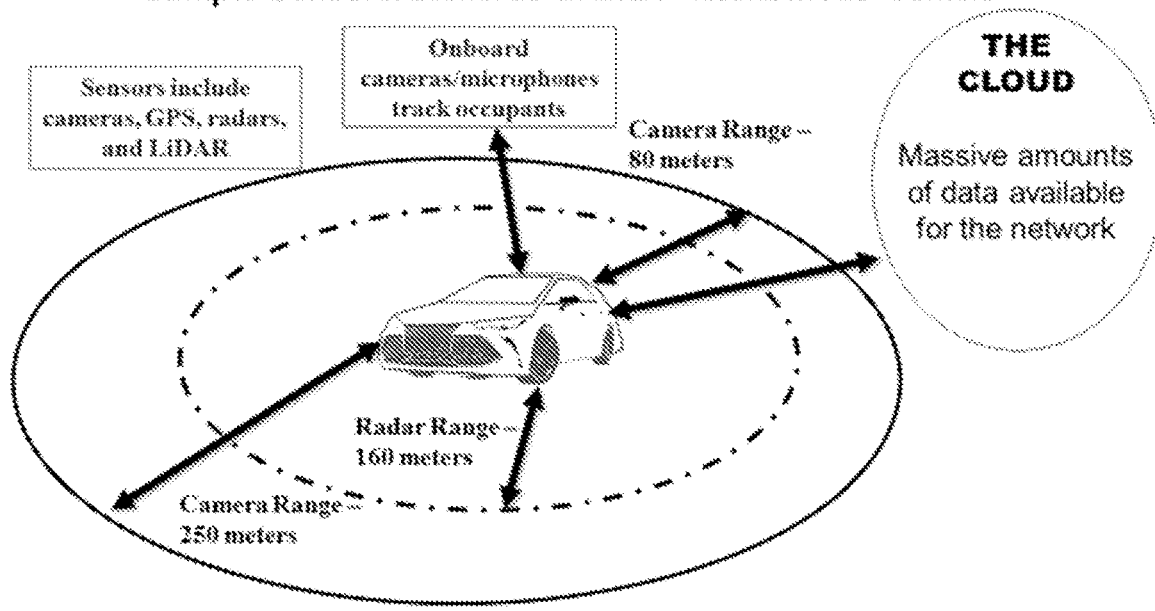
FIG. 2 Sample Sensors/Cameras in 2021 Autonomous Vehicles
FIG. 3 eCall is a good 1st Step the 2nd step is Big Data 911™
FIG. 4 that Big Data 911™ Monitors Drivers even with no Cell Network
FIG. 5 GPS/other Data from Millions of Vehicles/Phones sent to the Cloud Optimizing
FIG. 6 Our Skydiving Technology

FIG. 2 shows that autonomous vehicles use a large number of cameras, radars, and LiDAR to map the world around the vehicle and thereby plan the optimal, safe drive. In 2021, the industry leader Tesla used 8 cameras with 360 degrees of view with a range of up to 250 meters in front and 50 meters behind, while ultrasonic sensors enhanced the mapping around the car and radar even permitted seeing ahead even during rain, or in the fog or with dust.

However, internal cameras used to monitor the driver's condition have created some controversy. These internal cameras record and upload to the cloud the driver's actions prior to a crash. While the user can opt-out of this option, this is creating privacy concerns.

Figure 3:
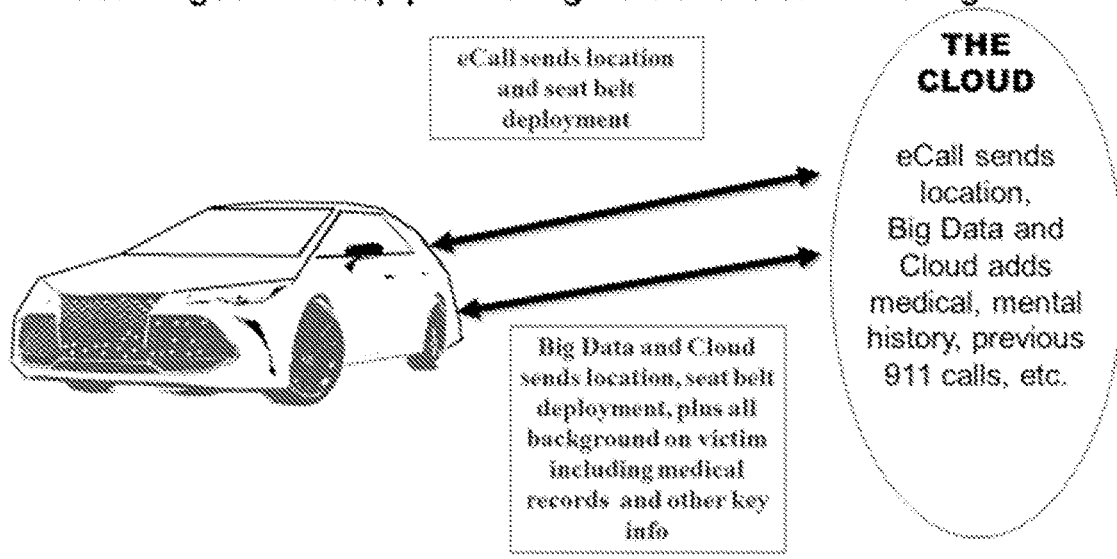

Automated Emergency calls are mandated in the EU and should be required in the U.S. FIG. 3—Telematics is a tracking device in vehicles which sends key information such as location, speed and harsh braking or acceleration. Up to 10 percent of drivers in the US use this technology since insurance companies offer discounts for sharing this data. However, in 2021 the European Union was far ahead of the US since after April 2018 all European Car Makers have been required to include eCall, an automated emergency call technology. When a crash is occurring eCall automatically sends the location and also indicates if the airbags were deployed. This is a good prototype of the system covered by this patent since Big Data with facial and voice recognition would identify the driver's ID, medical history and all relevant information needed to treat the victim.

Track Me—Option in Sporadic Cell Phone Coverage Areas

Figure 4:
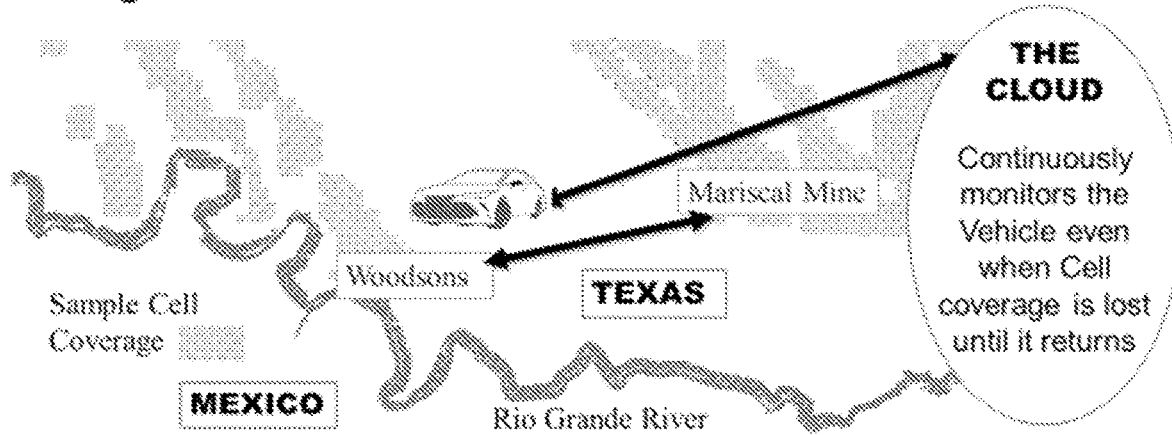

FIG. 4—One of the most remote areas in the lower 48 states is the Frank Church-River of No Return Wilderness in Idaho which has 2.37 million acres. It almost limited if any cell phone coverage. For example, Dixie Idaho (2019 population, 3,237) is near this area had limited cell coverage (2019). Large areas in Alaska have almost no coverage. The drive from Woodsons, Texas which is inside Big Bend National Park, to the Mariscal Mine, which is also in Big Bend, illustrates the problem and solution. This 11-mile drive takes roughly 55 minutes and has sporadic cell coverage. In Big Bend, wilderness areas and many National Parks, there should be the telematics option to turn on an optional Track Me where Big Data 911™ monitors the status of those vehicles which have lost cell coverage. After a pre-determined time, it would make an automatic phone call to confirm that the driver was OK. And then after a specified time even a 911 call could be made. This option could also be valuable when there was equipment failure on board the vehicle or a breakdown of part of a cell network.

Hundreds of Lives saved each year—AACN uses (1) sensors such as accelerometers, air bag deployment etc. to detect crashes and (2) it uses GPS for location only, not to determine where crashes occur. While AACN is powerful—it's more expensive requiring multiple sensors which drain power. Also, GPS without error-correcting doesn't provide accurate enough data. Big Data 911 is unique because it only needs error-corrected GPS's calculated acceleration/deceleration to determine a crash. The US DOT (AACN Research Report (No. DOT HS 812 729), 2019, May) estimated AACN saves 360 where AACN's benefits exceeded costs by $2.18 billion but only if it is used on millions of vehicles where it saves roughly 1 life per million vehicles. Big Data 911 using only GPS data could save lives when there's no AACN on a vehicle, or in other situations such as skydives. Assuming that up to 33% of vehicles either lacked AACN or Big Data 911 provided redundancy predicting crashes, Big Data 911 could save 120 lives per year, a net benefit of $0.72 billion.

Figure 5:
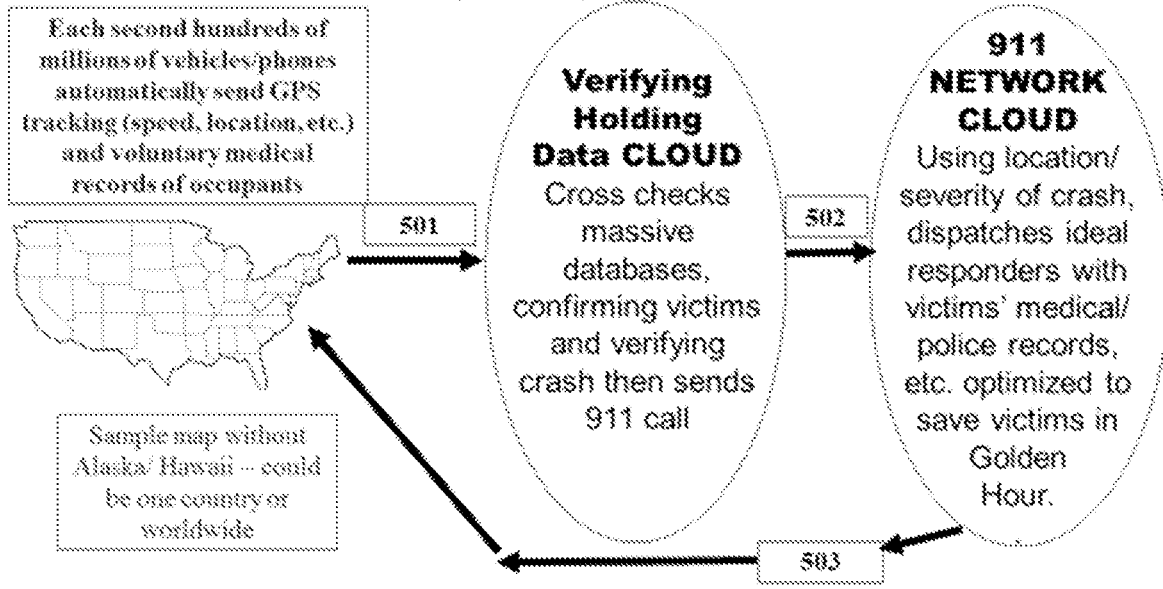

FIG. 5. 501—This figure shows how the system saves hundreds of lives each year as noted in the ACCN report but only by tracking the over 300 million vehicles in the U.S. The system sends info on millions of vehicles to the cloud optimizing the emergency response. The vehicle and/or phone app automatically sends its GPS location, speed, acceleration, and photos/voice and/or IDs of occupants plus any voluntary medical ID provided by the occupant. A phone can provide redundant GPS data which confirms the crash to the cloud in order to minimize the number of incorrect 911 calls. The cloud cross checks massive databases, including crash data and vehicles' crash data histories identifying occupants and optimizing response to save victims in Golden Hour.

In 2021, per the US Department of Transportation there were 276 million vehicles in the U.S. including 156 million trucks, 108 million cars, 8.5 million motorcycles, and 575 thousand buses. Statista data estimated that the USA has 280 million smartphone users in 2020. Redundancy in data sources reduces incorrect 911 calls. For example, if a person carried a cell phone on a motorcycle and dropped it this indicates a crash, however if there were an onboard tracking device on the motorcycle it would confirm the motorcycle didn't crash avoiding an unnecessary 911 call. For privacy concerns and to reduce storage requirements, this data could be constantly discarded since the only relevant data is actual crash and/or emergency data. FIG. 5 502 shows the data sent to a queue which uses AI (artificial intelligence and/or statistics), to verify that a crash has occurred. Finally, FIG. 5 503 the cloud reconfirms the GPS location and severity of crash, and dispatches ideal responders with victims' medical records, etc. optimized to save victims in Golden Hour.

Figure 6:
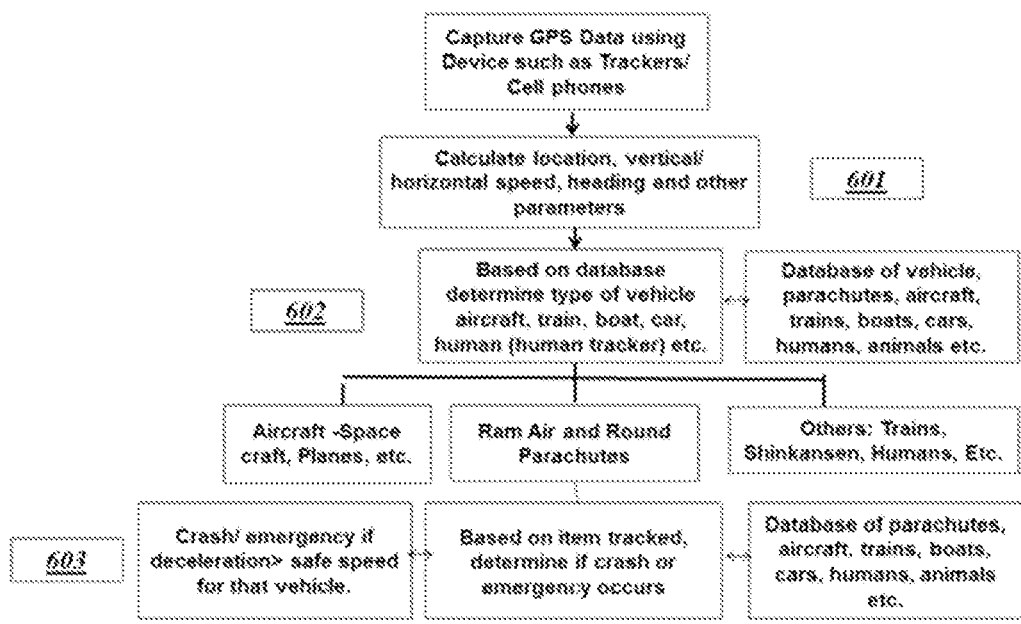

FIG. 6 show how our existing patent tracks data to identify the type of movement, i.e. aircraft, skydive etc., and correcting GPS data errors, such as lost data or corrupted data, and calculating the best angles and perspectives to view the plots in 3D interactive maps or videos which could be used for debriefings during accident investigations. The data is cross-checked with a database of many types of movements, from humans to trains, Round and Ram Parachutes, helicopters, Propeller Aircraft, Jet Aircraft and Spacecraft. Then the 3D interactive maps with the best angles for debriefings and accident investigations are automatically created.

What is claimed is:

1. A method using Big Data or cloud data to automatically use a communication unit and a GPS unit, such as a smart phone, and its GPS speed, acceleration/deceleration data, cross-checking excessive GPS acceleration/deceleration data with historical data to detect a crash and collect a victim's medical, psychological and driver history and prior 911 calls to expedite the response time by EMTs (Emergency Medical Technicians) for vehicle crashes and other emergencies focusing on the customized treatment of the victim during a Golden hour or beyond of an incident; monitoring via a call-taking computing device, a call from a caller reporting an incident of a given incident type; using information including caller ID, voice and facial recognition, prior 911 calls to identify the victim and provide appropriate medical treatment en route to a hospital and then continuing on after arrival at the hospital or medical facility;
tracking all vehicles which have lost vehicle and/or cell contact with the cloud to determine if an accident occurred and after a time period selected by a driver, automatically, optionally, calling the driver confirming their status and/or calling 911 if the loss of cell coverage exceeds a preset time limit.

2. The method of claim 1 further comprising: using caller ID and any cloud data, video and/or audio, which confirms the caller, injured party's identity to retrieve prior medical history, police reports and all relevant data to understand the subject's prior medical, mental history in order to immediately begin the appropriate care and response associated with the incident-type profile for the call; and using Advanced Automatic Collision Notification (AACN) and the injury severity score (ISS) to improve post-crash medical care.

3. A system comprising: a communication unit and a GPS unit, such as a smart phone or satellite phone device to monitor a vehicle's GPS elevation, location, acceleration, deceleration, speed and cross checking historical crash data and correcting for GPS data anomalies including lost or corrupted GPS signals, or loss of power, by cross-checking with prior GPS data creating clean GPS data to determine if an emergency condition exists including a crash, fire or other emergency and to then send a distress call to request the dispatch of EMT and/or police to the incident with all related medical information and other records of the potentially injured party;

further comprising tracking all vehicles which have lost vehicle and/or cell contact with the cloud to determine if an accident occurred and after a time period selected by a driver, automatically, optionally, calling the driver confirming their status and/or calling 911 if the loss of cell coverage exceeds a preset time limit.

4. The system of claim 3 further comprising an optional link, for redundancy, to a vehicle's on-board including Advanced Automatic Collision Notification (AACN) sensors, to monitor the vehicle's location, acceleration, deceleration, speed and the status of the vehicle's systems to determine if an emergency condition exists including a crash, fire or other emergency and to then send a distress call to request the dispatch of EMT and/or police to the incident with all related medical information and other records of the potentially injured party.

* * * * *